United States Patent
Haddock et al.

(10) Patent No.: US 10,485,656 B2
(45) Date of Patent: Nov. 26, 2019

(54) INTRAOCULAR LENS SYSTEM WITH FOLDING FEATURES

(71) Applicant: Verily Life Sciences LLC, Mountain View, CA (US)

(72) Inventors: Joshua N. Haddock, Mountain View, CA (US); Dimitri T. Azar, Chicago, IL (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 15/928,473

(22) Filed: Mar. 22, 2018

(65) Prior Publication Data

US 2018/0206980 A1    Jul. 26, 2018

Related U.S. Application Data

(62) Division of application No. 14/945,261, filed on Nov. 18, 2015, now Pat. No. 9,956,073.

(51) Int. Cl.
*A61F 2/16*    (2006.01)

(52) U.S. Cl.
CPC .......... *A61F 2/1648* (2013.01); *A61F 2/1624* (2013.01); *A61F 2002/169053* (2015.04); *A61F 2250/0001* (2013.01); *A61F 2250/0029* (2013.01)

(58) Field of Classification Search
CPC .... A61F 2/1624; A61F 2/1648; A61F 2/1613; A61F 2002/169053; A61F 2250/0001; G02C 7/04; G02C 7/083
USPC ........................................................ 623/6.21
See application file for complete search history.

(56) References Cited

U.S. PATENT DOCUMENTS

| | | | |
|---|---|---|---|
| 4,608,049 A | | 8/1986 | Kelman |
| 4,657,546 A | * | 4/1987 | Shearing ............... A61F 2/1648 623/6.21 |
| 4,704,124 A | | 11/1987 | Shearing |
| 4,725,278 A | * | 2/1988 | Shearing ............... A61F 2/1613 623/6.21 |
| 4,834,754 A | * | 5/1989 | Shearing ............... A61F 2/1648 623/6.21 |
| 4,878,912 A | | 11/1989 | Castleman |

(Continued)

FOREIGN PATENT DOCUMENTS

WO    97/43984 A1    11/1997

OTHER PUBLICATIONS

International Preliminary Report on Patentability with Written Opinion dated May 22, 2018, for International Application No. PCT/US2016/057132, filed Oct. 14, 2016, 8 pages.

(Continued)

*Primary Examiner* — David H Willse
*Assistant Examiner* — Tiffany P Shipmon
(74) *Attorney, Agent, or Firm* — Christensen O'Connor Johnson Kindness PLLC

(57) ABSTRACT

A method of folding and unfolding an active accommodating intraocular lens system includes folding an active lens element along at least one folding line. The at least one folding line is defined by mechanical indentations disposed on a perimeter of the active lens element, and a first pair of the mechanical indentations define terminal ends of a first folding line extending between the first pair of the mechanical indentations. The active lens element is unfolded.

16 Claims, 6 Drawing Sheets

FOLD PATTERNS

(56) References Cited

U.S. PATENT DOCUMENTS

| | | | |
|---|---|---|---|
| 5,171,319 A | 12/1992 | Keates et al. | |
| 9,155,614 B2 | 10/2015 | Blum et al. | |
| 2011/0015733 A1* | 1/2011 | Schnell | A61F 2/1616 623/6.18 |
| 2011/0137391 A1 | 6/2011 | Leigh | |
| 2013/0245754 A1* | 9/2013 | Blum | A61F 2/1627 623/6.13 |
| 2015/0216652 A1* | 8/2015 | Jansen | A61F 2/1613 623/6.43 |
| 2015/0272727 A1 | 10/2015 | Humayun et al. | |

OTHER PUBLICATIONS

International Search Report and Written Opinion from the International Searching Authority dated Dec. 23, 2016 or International Application No. PCT/US2016/057132, filed Oct. 14, 2016, 16 pages.
Australian First Examination Report dated Jun. 25, 2018 for Australian Application No. 2016355060, filed Nov. 14, 2016, 4 pages.
First Office Action for Chinese Patent Application No. 201680067316.X, dated Apr. 30, 2019, 22 pages.

* cited by examiner

INTRAOCULAR LENS SYSTEM WITH FOLDING FEATURES

CROSS-REFERENCE TO RELATED APPLICATIONS

This application is a divisional of U.S. application Ser. No. 14/945,261, filed Nov. 18, 2015, the contents of which are incorporated herein by reference.

TECHNICAL FIELD

This disclosure relates generally to intraocular lenses, and in particular but not exclusively, relates to active accommodating intraocular lens systems.

BACKGROUND INFORMATION

Intraocular lenses (IOLs) are used to treat a wide variety of physical maladies including near-sightedness, far-sightedness, astigmatism, and cataracts. IOLs are placed within an eye by cutting the eye open and inserting the IOL. Typically an IOL includes a small lens with side struts, called haptics, which are used to hold the lens in place inside the eye.

IOL insertion for the treatment of cataracts is a common ophthalmological surgical procedures in the United States and around the world. The procedure is frequently completed under local anesthesia and usually takes less than 30 minutes. Furthermore, the recovery time is relatively short (approximately 2-3 weeks). However, one major disadvantage associated with cataracts lens replacement surgery, and the conventional IOLs used, is that IOLs are typically only focused for long distance sight. While patients who undergo standard IOL implantation no longer experience cloudy vision from cataracts, they largely lose their ability to accommodate (change the focal length of their eye(s) from near to far).

To remedy this problem, accommodating IOLs have been developed that incorporate an active focusing optic to mimic the natural accommodative process. While these accommodating IOLs offer significant improvement over their non-accommodating counterparts, rarely does the vision of the person receiving the lens return to the pre-cataracts natural-lens state.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus and method for an active accommodating intraocular lens system are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
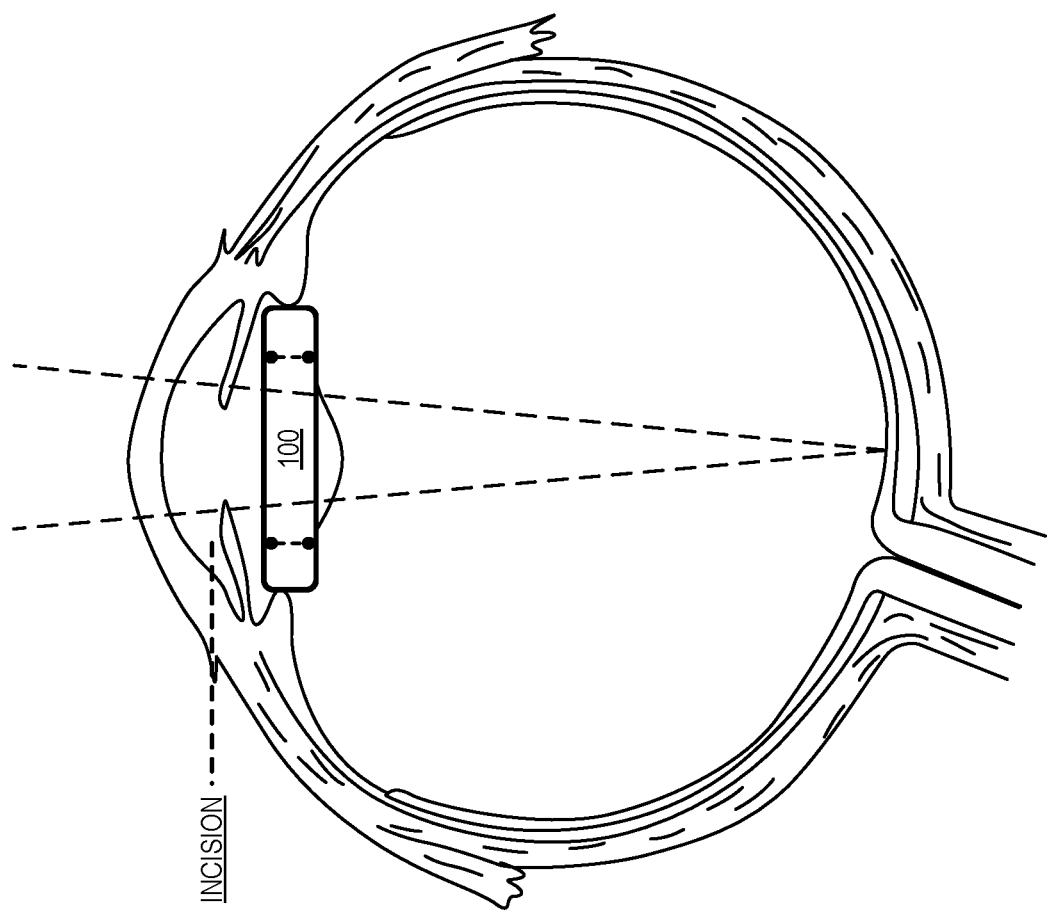
FIG. 1 is a cross sectional illustration of an eye including an intraocular lens system, in accordance with an embodiment of the disclosure.

FIG. 1 is a cross sectional illustration of an eye including an intraocular lens (IOL) system 100, in accordance with an embodiment of the disclosure. In the depicted embodiment, IOL system 100 has been inserted into the eye to replace the eye's natural lens which may have been removed for a variety of reasons including cataracts surgery. In operation, IOL system 100 works to provide optical accommodation by employing one or more microelectronic and/or optical devices that allow the eye to readily focus on different focal distances. These microelectronic and/or optical devices may be disposed in/on a lens or may include a physically distinct lens controller system. In one embodiment, IOL system 100 includes a lens with a liquid crystal optical component that utilizes variable optical power for dynamic accommodation control. In one embodiment, a microelectronic control system is disposed along the perimeter of the lens to control the liquid crystal optical component. It should be noted that while IOL system 100 is useful to remedy problems associated with accommodation, it may also be used to solve other problems and may even be used to enhance eyesight beyond natural constraints.

In the depicted example, IOL system 100 is surgically implanted into the eye. Limiting the size of the incision is important in order to reduce surgical recovery time and minimize the chance of post-surgical complications which may impact the patient's vision. Accordingly, the lens element of IOL system 100 may be folded such that the cross-sectional area of IOL system 100 is reduced as it is inserted into the eye. By folding IOL system 100 the surgeon may make a much smaller incision than would otherwise be required.

Figure 2:
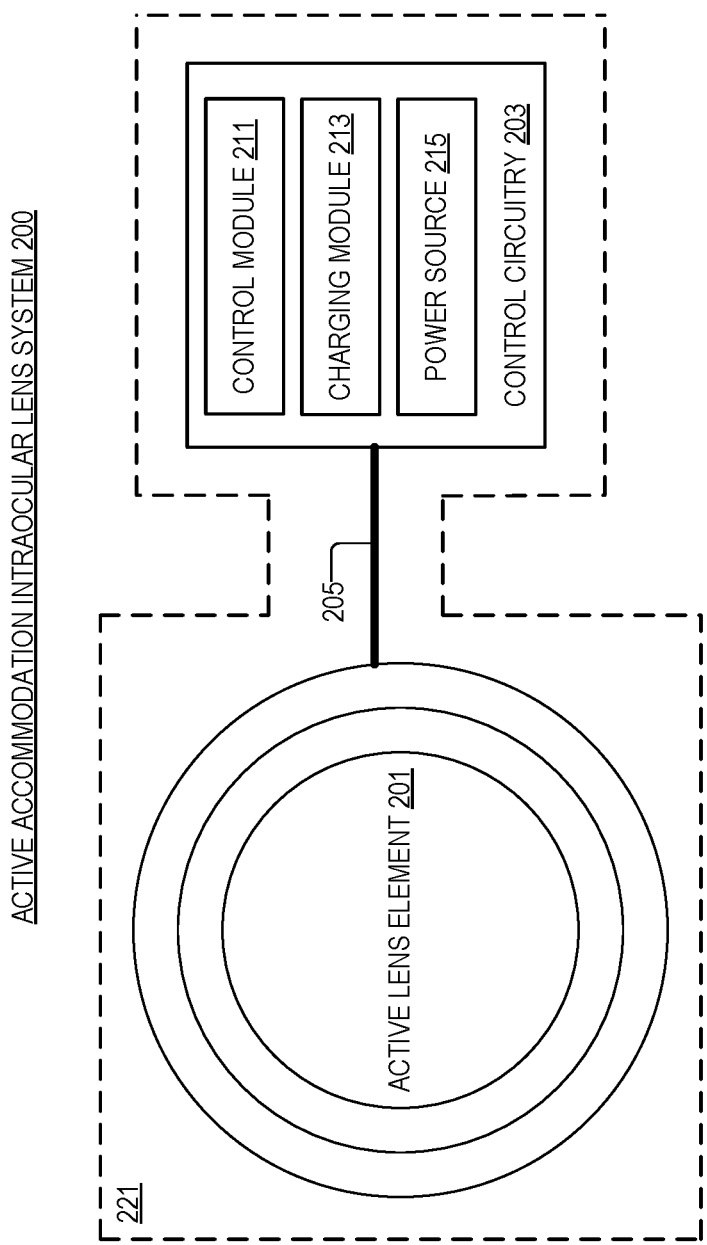
FIG. 2 illustrates a functional block diagram of an active accommodating intraocular lens system, in accordance with an embodiment of the disclosure.

FIG. 2 illustrates a functional block diagram of an active accommodating intraocular lens system 200, in accordance with an embodiment of the disclosure. The illustrated embodiment of active accommodating IOL system 200 includes active lens element 201, control circuitry 203, encapsulation layer 221, and conductive tether 205. The illustrated embodiment of control circuitry 203 includes control module 211, charging module 213, and power source 215. Active lens element 201 provides dynamic optical power for active accommodation, and is coupled to control circuitry 203 which controls active lens element 201 during the active accommodation process. In the depicted embodiment, control circuitry 203 is separate from active lens element 201 and is coupled via a conductive tether 205. However, in another embodiment, control circuitry 203 may be physically included in/on active lens element 201 or immediately adjacent thereto. Control circuitry 203 may be disposed along the periphery of active lens element 201 to avoid interference with optical accommodation devices that may be disposed in the center of active lens element 201. In one embodiment, active lens element 201 may include liquid crystal devices in the center of active lens element 201. In another embodiment, active lens element 201 may include fluidic devices, electrowetting devices, microelectromechanical (MEMS) devices, or the like in the center of active lens element 201 which change their optical power dynamically to adjust for the best focus for the patient.

Control circuitry 203 may contain a variety of sub elements including control module 211. In the depicted embodiment, control module 211 is coupled to control active lens element 201. In one embodiment, control logic in control module 211 is implemented as hardware logic (e.g. ASIC, FPCA, etc.) and/or firmware instructions. However, in another embodiment control logic may be implemented in software (which can be altered after active accommodating IOL system 200 has been inserted into the eye), or a combination of hardware and software. Power source 215 is coupled to provide power to both control module 211 and active lens element 201. In one embodiment, power source 215 includes a battery such as a lithium ion battery or the like. In another embodiment, power source 215 may include a capacitor. Power source 215 is coupled to charging module 213 which provides charge to the power source 215. In one embodiment, charging module 213 may contain a photovoltaic device. In another embodiment, charging module 213 includes an inductive charging system. The inductive charging system may receive electromagnetic radiation and convert the electromagnetic radiation into charge via induction. Once active accommodating IOL system 200 has been successfully inserted into the eye, charging module 213 may receive electromagnetic radiation from an inductive charging apparatus. The user of the active accommodating IOL system 200 may be notified of a low-power situation by a display in active lens element 201, prompting the user to use the charging apparatus. Additionally, the active accommodating IOL system 200 may communicate with the charging apparatus via a variety of electromagnetic transmission technologies including backscatter radio-frequency identification, or the like. In this manner, software installed on the active accommodating IOL system 200 may be updated.

In the depicted embodiment, active accommodating IOL system 200 is encased in encapsulation layer 221. Encapsulation layer 221 is disposed on an outer surface of active accommodating IOL system 200. Encapsulation layer 221 may include a single layer or many layers of encapsulant that is spray coated, dip coated, or the like onto active accommodating IOL system 200. Furthermore, encapsulation layer 221 may cover all, or only some of, active accommodating IOL system 200. In one embodiment, encapsulation layer 221 includes a bio-compatible polymer material such as: silicone, polyethylene, polypropylene, polymethymethacrylate, polyethyleneoxide, polyvinylalcohol, or otherwise.

FIGS. 3A-3E illustrate a variety of fold lines 309 and mechanical indentation 307 patterns that can be implemented with active lens element 301, in accordance with several embodiments of the disclosure. During implantation of the active accommodating IOL system (e.g. active accommodating IOL system 200), an incision is made in the receiving eye. In order to reduce the length of the incision, active lens element 301 is folded to reduce its cross-sectional area. To facilitate folding, mechanical indentations 307 are made along a perimeter of the active lens element 301. The mechanical indentations 307 form structurally weakened locations in the active lens element 301. These mechanical indentations 307 allow for the ophthalmic surgeon to fold active lens element 301 along predetermined folding lines 309.

Figure 3A:
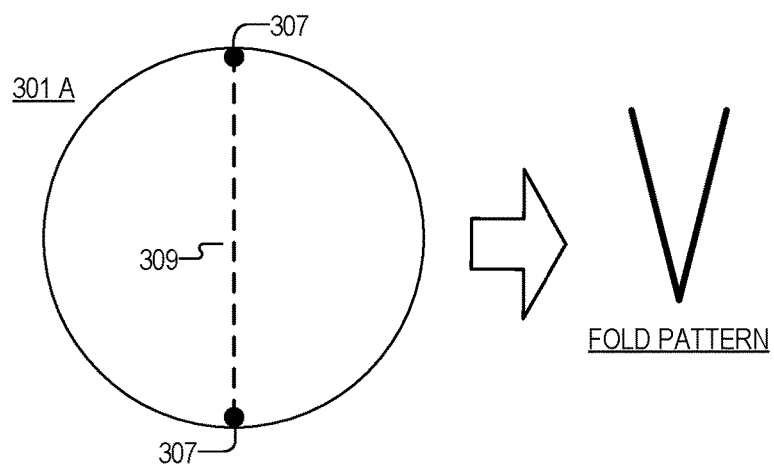
FIGS. 3A-3E illustrate a variety of fold and mechanical indentation patterns that can be implemented with an active lens element, in accordance with several embodiments of the disclosure.

FIG. 3A illustrates one embodiment of active lens element 301 where a first pair of mechanical indentations 307 define terminal ends of a first folding line 309. This first pair of mechanical indentations 307 promotes folding of the active lens element 301 along first folding line 309. In the depicted embodiment, the first pair of mechanical indentations 307 is positioned along the perimeter of active lens element 301 so that first folding line 309 symmetrically bisects active lens element 301 in half.

Figure 3B:
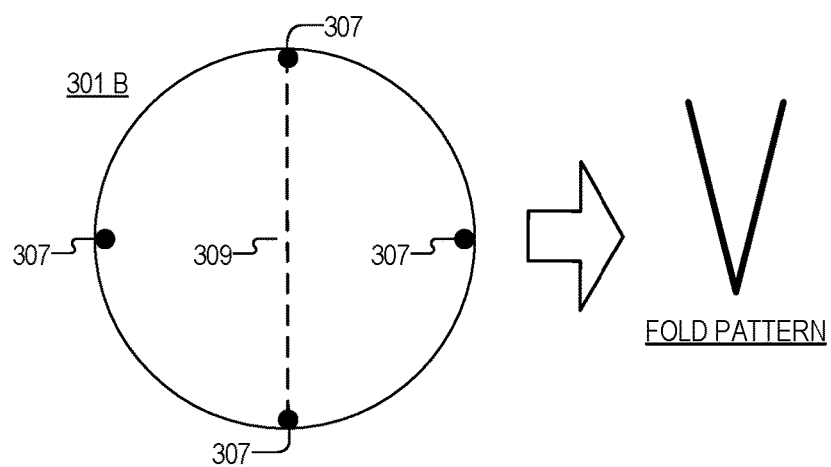

FIG. 3B illustrates one embodiment of active lens element 301 where a first pair of mechanical indentations 307 define terminal ends of a first folding line 309. The first pair of mechanical indentations 307 promotes folding of the active lens element 301 along first folding line 309. The depicted embodiment also shows a second pair of mechanical indentations 307 which are positioned to provide symmetry of mechanical indentations 307. It is believed that symmetry of optical defects/aberrations is preferable in vision correction devices and procedures. It is worth noting that in at least one embodiment of the present disclosure; the length along the perimeter of active lens element 301 between all adjacent mechanical indentations 307 is equal to provide symmetry of optical aberrations that may be induced by said indentations.

Figure 3C:
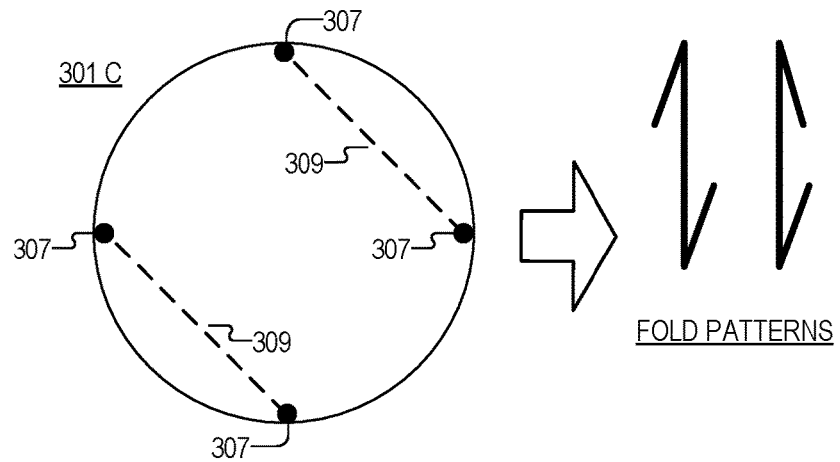

FIG. 3C illustrates one embodiment of active lens element 301 where active lens element 301 is folded into three sections to further reduce the size of the incision in the eye. In the depicted embodiment, a first pair of mechanical indentations 307 and a second pair of mechanical indentations 307 are positioned on the perimeter of active lens element 301. The first pair of mechanical indentations 307 and the second pair of mechanical indentations 307 define terminal ends of a first folding line 309 and a second folding line 309, respectively. The first folding line 309 and the second folding line 309 extend between the first pair of mechanical indentations 307 and the second pair of mechanical indentations 307 and promote folding of the active lens element 301. In one embodiment, the length along the perimeter of active lens element 301 between all mechanical indentations 307 is equal to provide symmetry of optical aberrations that may be induced by said indentations.

Figure 3D:
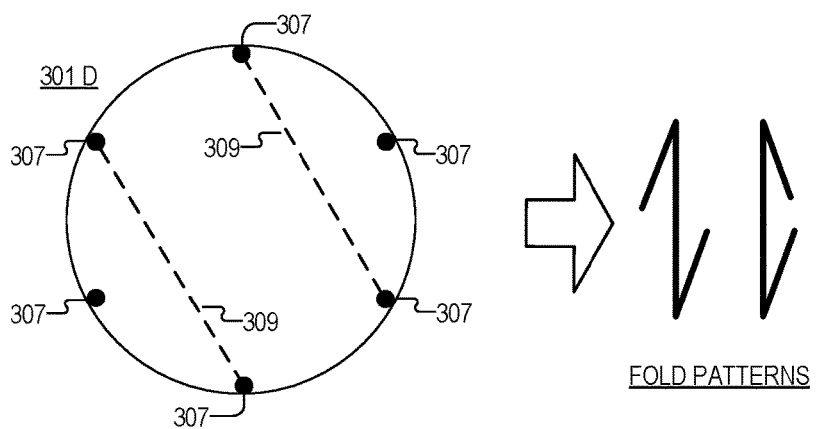

FIG. 3D illustrates one embodiment of active lens element 301 where active lens element 301 is again folded into three sections. In the depicted embodiment, a first pair of mechanical indentations 307, a second pair of mechanical indentations 307, and a third pair of mechanical indentations 307 are positioned on the perimeter of active lens element 301. The first pair of mechanical indentations 307 and the second pair of mechanical indentations 307 define terminal ends of a first folding line 309 and a second folding line 309, respectively. The first folding line 309 and the second folding line 309 extend between the first pair of mechanical indentations 307 and the second pair of mechanical indentations 307 and promote folding of the active lens element 301. In one embodiment, a length along the perimeter of active lens element 301 between all adjacent mechanical indentations 307 is equal. In the depicted embodiment, one mechanical indentation 307 (from the third pair of mechanical indentations 307) is disposed along the perimeter of active lens element 301 between the terminal ends of the first folding line 309 and between the terminal ends of the second folding line 309. In one embodiment, the third pair of mechanical indentations 307 is disposed to provide symmetry of mechanical indentations 307.

Figure 3E:
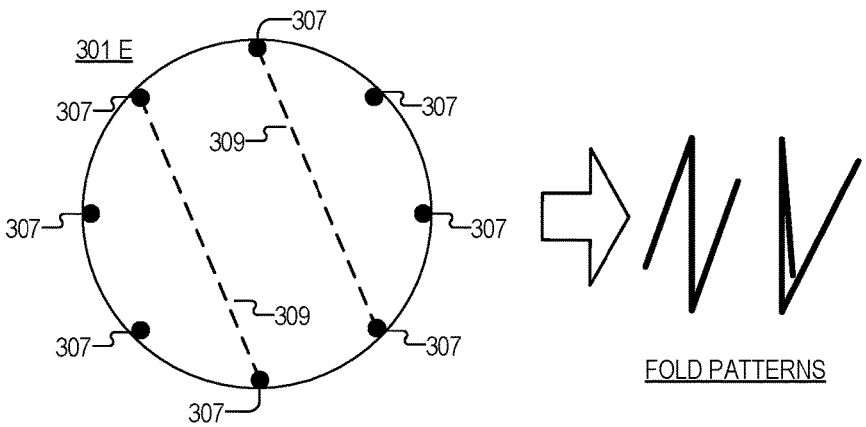

FIG. 3E illustrates one embodiment of active lens element 301 where active lens element 301 is folded into three sections. In the depicted embodiment, a first pair of mechanical indentations 307, a second pair of mechanical indentations 307, a third pair of mechanical indentations 307, and a fourth pair of mechanical indentations 307 are positioned on the perimeter of active lens element 301. The first pair of mechanical indentations 307 and the second pair of mechanical indentations 307 define terminal ends of a first folding line 309 and a second folding line 309, respectively. The first folding line 309 and the second folding line 309 extend between the first pair of mechanical indentations 307 and the second pair of mechanical indentations 307 and promote folding of the active lens element 301. In one embodiment, a length along the perimeter of active lens element 301 between all adjacent mechanical indentations 307 is equal. In the depicted embodiment, two mechanical indentations 307 (from the third pair and the fourth pair of mechanical indentations 307) are disposed along the perimeter of active lens element 301 between the terminal ends of the first folding line 309 and between the terminal ends of the second folding line 309. In one embodiment, the third pair of mechanical indentations 307 and the fourth pair of mechanical indentations 307 are disposed to provide symmetry of mechanical indentations 307.

In several embodiments not depicted, mechanical indentations 307 may extend from the perimeter of active lens element 301 towards the center of active lens element 301 a majority of the distance to the center of active lens element 301. In several embodiments, mechanical indentations 307 may extend from the perimeter of active lens element 301 towards the center of active lens element 301 a length such that mechanical indentations 307 do not contact the optical devices in active lens element 301. In this way, optical distortion resulting from mechanical indentations 307 is reduced. In several embodiments, where active lens element 301 is circular, mechanical indentations 307 may be relatively large and extend from the perimeter of active lens element 301 towards the center of active lens element 301 a length that is 45% or less of the radius of active lens element 301. In other embodiments, mechanical indentations 307 may be relatively small and extend from the perimeter of active lens element 301 towards the center of active lens element 301 a length that is 5% or less of the radius of active lens element 301. Further, mechanical indentations 307 may be wider than they are long, longer than they are wide, or length and width may be equal. In some embodiments, mechanical indentations 307 may extend through the bulk of active lens element 301 (creating a hole in active lens element 301), or may only extend through part of active lens element 301 (creating a divot in active lens element 301).

Additionally, the depth of mechanical indentations 307 may vary as a function of location on active lens element 301.

Although the embodiments depicted in FIGS. 3A-3E show even numbers of mechanical indentations 307, in several embodiments not depicted, an odd number of mechanical indentations 307 may be positioned on the perimeter of active lens element 301. Odd or even number mechanical indentations 307 may have consistent indentation geometry on the same active lens element 301, or indentation geometry that differs between mechanical indentations 307 on the same active lens element 301. Additionally, in some embodiments of the active accommodating IOL system, more than two folding lines 309 may be disposed on active lens element 301. Folding lines 309 do not necessarily have to be parallel to one another and may even bisect other folding lines 309. Furthermore, active lens element 301 does not necessarily have to be circular. Active lens element 301 may take the shape of a rectangle, hexagon, octagon, or other polygon. Furthermore, mechanical indentations 307 may be disposed on active lens element 301 such that they are disposed on an encapsulation layer (e.g. encapsulation layer 221) encasing active lens element 301.

Figure 4A:
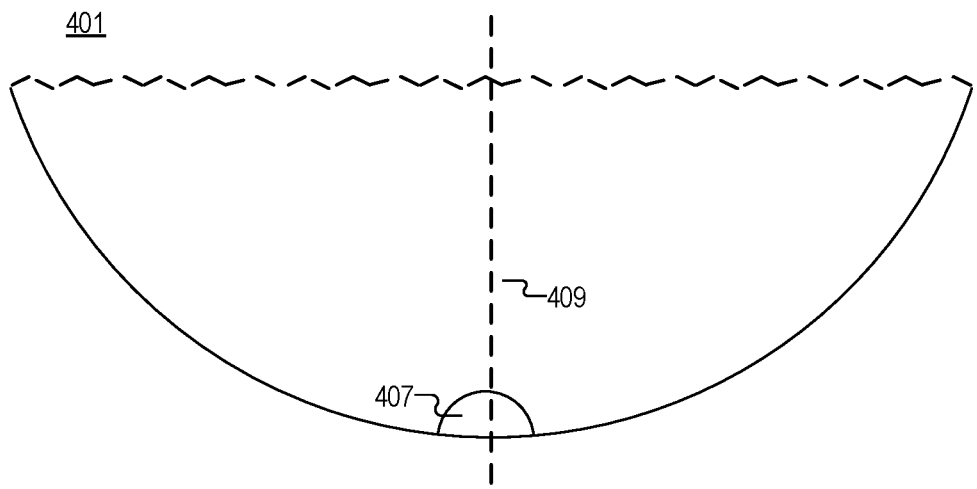
FIG. 4A is a top-down illustration of a mechanical indentation on an active lens element, in accordance with an embodiment of the disclosure.

FIG. 4A is a top-down illustration of a mechanical indentation 407 on an active lens element 401, in accordance with an embodiment of the disclosure. In the depicted example, mechanical indentation 407 is rounded and does not extend through or across active lens element 401. However, in another embodiment, mechanical indentation 407 may not be rounded, and may extend through active lens element 401. Additionally, mechanical indentation 407 may extend across active lens element 401 any distance along folding line 409.

Figure 4B:
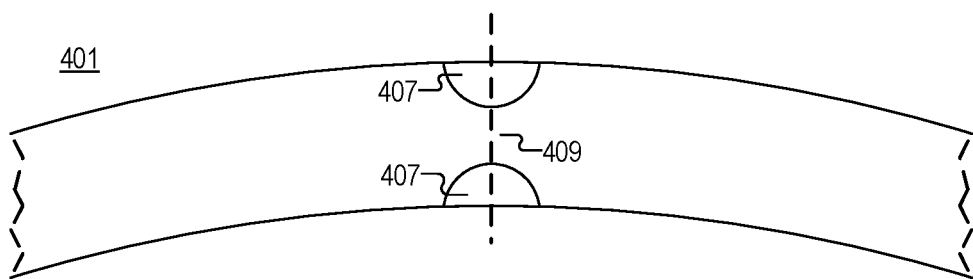
FIG. 4B is a side view illustration of the mechanical indentation in FIG. 4A, in accordance with an embodiment of the disclosure.

FIG. 4B is a side view illustration of the mechanical indentation in FIG. 4A, in accordance with an embodiment of the disclosure. In the depicted embodiment, a single mechanical indentation 407 includes two score marks in the frontside and backside of active lens element 401. Although the depicted embodiment shows two score marks with identical geometry, in one or more embodiments, the score mark on the frontside of active lens element 401 may have a different indentation geometry than the score mark on the backside of active lens element 401. This may useful during folding since one of the score marks may experience tensile stress where the other experiences compressive stress. In other embodiments, mechanical indentation 407 can be made from a single score mark on the frontside or the backside of active lens element 401, or may extend through active lens element 401. Additionally, mechanical indentations 407 may be disposed on an outer edge of active lens element 401. Mechanical indentation 407 may take the form of: a score, a divot, a cut, a mark, an inclusion, a perforation, a thinning, and/or a weakening. Mechanical indentations 407, may be rounded or have corners.

Figure 5:
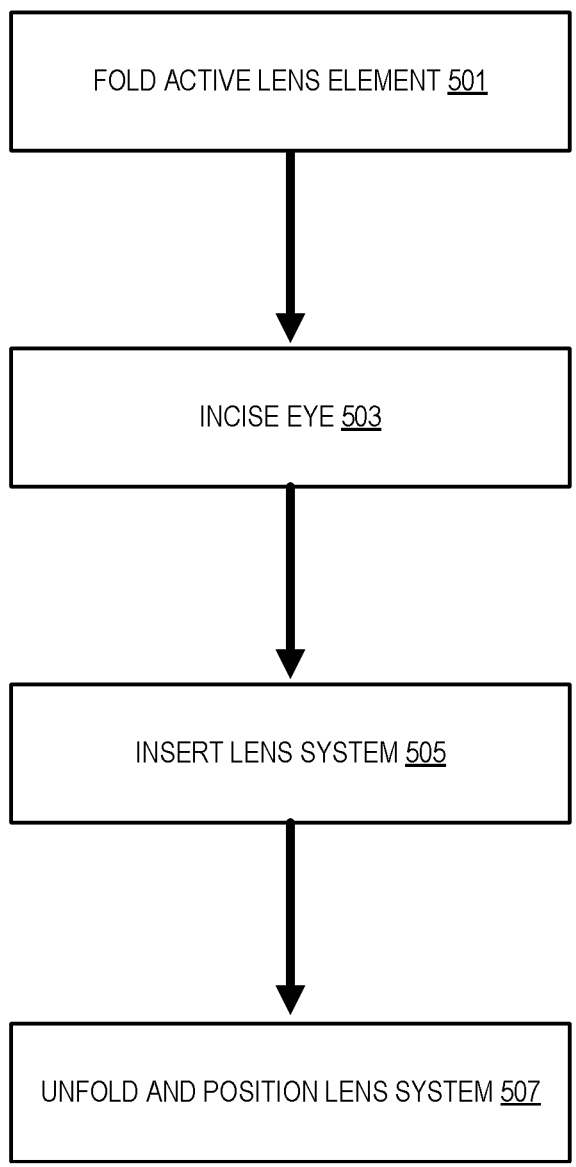
FIG. 5 is a flow chart for a method of inserting an active accommodating intraocular lens system into an eye, in accordance with an embodiment of the disclosure.

FIG. 5 is a flow chart 500 for a method of inserting an active accommodating intraocular lens system (e.g. active accommodating IOL system 200) into an eye, in accordance with an embodiment of the disclosure. The order in which some or all of the method blocks appear should not be deemed limiting. Rather, one of ordinary skill in the art having the benefit of the present disclosure will understand that some of the method blocks may be executed in a variety of orders not illustrated, or even in parallel.

Method block 501 details folding the active lens element (e.g. active lens element 301). This reduces the size of the incision necessary to insert and place the active accommodating IOL system into the eye. Folding the active lens element may include folding the active lens element along at least one fold line where the at least one fold line is defined by mechanical indentations disposed on a perimeter of the active lens element. A first pair of the mechanical indentations may be used to define terminal ends of a first fold line extending between the first pair of the mechanical indentations.

Method block 503 provides for incising the eye to insert the active accommodating intraocular lens system into the eye. In order to reduce recovery time and minimize the probability of surgical complication, it is important to make the smallest incision possible. Hence, folding the active lens element helps achieve this goal by allowing the accommodating IOL system to fit through a smaller incision.

Method block 505 provides for inserting the active accommodating IOL system into the eye. After incising the eye, the ophthalmic surgeon slides the folded active accommodating IOL system into the eye through the incision. Depending on the fold pattern of the device, incision geometry can be tailored to minimize recovery time.

Method block 507 details unfolding and positioning the active accommodating IOL system in the eye. This requires the surgeon to place the accommodating IOL system in the proper compartment within the eye and ensure that it has been fully unfolded such that light can properly pass through the intraocular lens. In one embodiment, the active lens element may include two flexible struts ("haptics") acting like tension springs to center the active lens element within the proper eye compartment.

In some embodiments of the method not depicted, the surgeon or patient may charge the active accommodating intraocular lens system within the eye. A charging system may be electrically coupled to the control circuitry in the IOL device to receive electromagnetic radiation and convert the electromagnetic radiation into charge via an inductive process. The charging system may be disposed in the active lens element itself or may physically separate from the active lens element.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method of creating an intraocular lens (IOL) system, comprising:
   forming an active lens element to provide dynamic optical power; and
   creating mechanical indentations disposed along a perimeter of the active lens element, wherein the mechanical indentations form structurally weakened locations in the active lens element, wherein a first pair of the mechanical indentations define terminal ends of a first folding line extending between the first pair of the mechanical indentations, and wherein the first pair of the mechanical indentations promote folding of the active lens element along the first folding line.

2. The method of claim 1, wherein creating the mechanical indentations includes at least one of scoring, cutting, marking, perforating, thinning, or weakening the active lens element.

3. The method of claim 1, wherein creating the first pair of the mechanical indentations includes positioning the first pair of mechanical indentations along the perimeter of the active lens element so that the first folding line symmetrically bisects the active lens element in half.

4. The method of claim 1, further comprising creating a second pair of the mechanical indentations, wherein a length along the perimeter of the active lens element between all adjacent mechanical indentations is equal.

5. The method of claim 1, further comprising forming an optical device disposed proximate to a center of the active lens element to provide the dynamic optical power.

6. The method of claim 5, further comprising forming control circuitry coupled to the optical device to control the dynamic optical power, wherein the optical device includes liquid crystal.

7. The method of claim 1, wherein forming the active lens element includes forming an encapsulation layer that encapsulates the active lens element by at least one of spray coating or dip coating.

8. The method of claim 7, wherein the forming the encapsulation layer includes at least one of using silicone, polyethylene, polypropylene, polymethymethacrylate, polyethyleneoxide, or polyvinylalcohol.

9. The method of claim 1, wherein the mechanical indentations include a plurality of indentation pairs, including the first pair.

10. The method of claim 9, wherein each of the plurality of indentation pairs are disposed along the perimeter of the active lens element, and wherein each of the mechanical indentations are separated from each other one of the mechanical indentations such that a length along the perimeter of the active lens element between any two adjacent ones of the mechanical indentations is equal.

11. The method of claim 1, wherein each of the mechanical indentations, including the first pair, are separated from each other one of the mechanical indentations such that a length along the perimeter of the active lens element between any two adjacent ones of the mechanical indentations is equal.

12. The method of claim 1, wherein at least one of the mechanical indentations is offset from an optical device disposed proximate to a center of the active lens element and extends partially from the perimeter of the active lens element towards the center of the active lens element.

13. The method of claim 12, wherein a length of the at least one of the mechanical indentations is 45% or less of a radius of the active lens element.

14. The method of claim 12, wherein a length of the at least one of the mechanical indentations is 5% or less of a radius of the active lens element.

15. The method of claim 1, wherein at least one of the mechanical indentations does not extend through a thickness of the active lens element.

16. The method of claim 15, wherein the at least one of the mechanical indentations indents a front side and a back side of the active lens element.

* * * * *